US012797063B2

(12) United States Patent
Gordon et al.

(10) Patent No.: US 12,797,063 B2
(45) Date of Patent: Nov. 17, 2026

(54) TISSUE-PIERCING IMPLANT

(71) Applicant: Teleflex Life Sciences LLC, Wilmington, DE (US)

(72) Inventors: Alexander Charles Gordon, San Carlos, CA (US); Curtis Yarra, Oakland, CA (US); Erik Noel, San Ramon, CA (US); Ernest Cabreza, Dublin, CA (US)

(73) Assignee: Teleflex Life Sciences LLC, Wilmington, DE (US)

( * ) Notice: Subject to any disclaimer, the term of this patent is extended or adjusted under 35 U.S.C. 154(b) by 43 days.

(21) Appl. No.: 19/085,965

(22) Filed: Mar. 20, 2025

(65) Prior Publication Data

US 2025/0295406 A1 Sep. 25, 2025

Related U.S. Application Data

(60) Provisional application No. 63/568,753, filed on Mar. 22, 2024.

(51) Int. Cl.
*A61B 17/04* (2006.01)
*A61B 17/06* (2006.01)

(52) U.S. Cl.
CPC .... *A61B 17/0401* (2013.01); *A61B 17/06166* (2013.01); *A61B 2017/0446* (2013.01)

(58) Field of Classification Search
CPC .......... A61B 17/0401; A61B 17/06166; A61B 2017/0446; A61B 2017/00274;
(Continued)

(56) References Cited

U.S. PATENT DOCUMENTS 4,898,156 A * 2/1990 Gatturna .............. A61F 2/0811 606/232
2005/0256530 A1 11/2005 Petros
(Continued)

FOREIGN PATENT DOCUMENTS

CN 105852938 A 8/2016
CN 109675177 A 4/2019

OTHER PUBLICATIONS

International Search Report and Written Opinion for International Application No. PCT/US2025/020769, dated May 26, 2025, 17 pgs.

*Primary Examiner* — Andrew Restaino
(74) *Attorney, Agent, or Firm* — Dorsey & Whitney LLP

(57) ABSTRACT

A prostatic implant configured to compress an enlarged prostate gland includes a distal anchor portion and a proximal end portion connected by a middle portion. The distal anchor portion includes a distal piercing portion and a proximal tail portion. The distal piercing portion includes a sharp distal tip configured to penetrate a lobe of the prostate gland, including the firm prostatic capsule. A tubular push member coupled with the prostatic implant advances the implant distally, led by the distal piercing portion, until the proximal tail portion is positioned outside the prostatic capsule, at which point the tubular push member is retracted proximally, unsheathing the distal anchor portion of the implant. The proximal tail portion is biased such that, upon exiting the tubular push member, the tail portion extends away from a longitudinal axis of the tubular push member, across the outer surface of the capsule.

17 Claims, 13 Drawing Sheets

(58) Field of Classification Search
CPC .... A61B 2017/0409; A61B 2017/0417; A61B 2017/0419; A61B 2017/0437; A61B 2017/0464
See application file for complete search history.

(56) References Cited

U.S. PATENT DOCUMENTS

| | | | | |
|---|---|---|---|---|
| 2006/0195008 | A1 | 8/2006 | Whalen et al. | |
| 2008/0039889 | A1* | 2/2008 | Lamson | A61B 17/00234 606/151 |
| 2008/0208355 | A1* | 8/2008 | Stack | A61B 17/064 623/23.65 |
| 2009/0112052 | A1* | 4/2009 | Lund | A61F 2/0045 128/898 |
| 2010/0191045 | A1 | 7/2010 | Gobron et al. | |
| 2010/0286717 | A1 | 11/2010 | Heinrich et al. | |
| 2011/0011917 | A1* | 1/2011 | Loulmet | A61F 2/2457 227/181.1 |
| 2011/0105841 | A1 | 5/2011 | Kutikov et al. | |
| 2011/0178537 | A1 | 7/2011 | Whitman | |
| 2013/0268001 | A1 | 10/2013 | Catanese et al. | |
| 2016/0022265 | A1 | 1/2016 | Kawaura et al. | |
| 2016/0095685 | A1 | 4/2016 | Vemuri et al. | |
| 2018/0103945 | A1 | 4/2018 | Ciulla et al. | |
| 2020/0146809 | A1* | 5/2020 | Petros | A61F 2/0805 |
| 2022/0125499 | A1 | 4/2022 | Hoey et al. | |

* cited by examiner

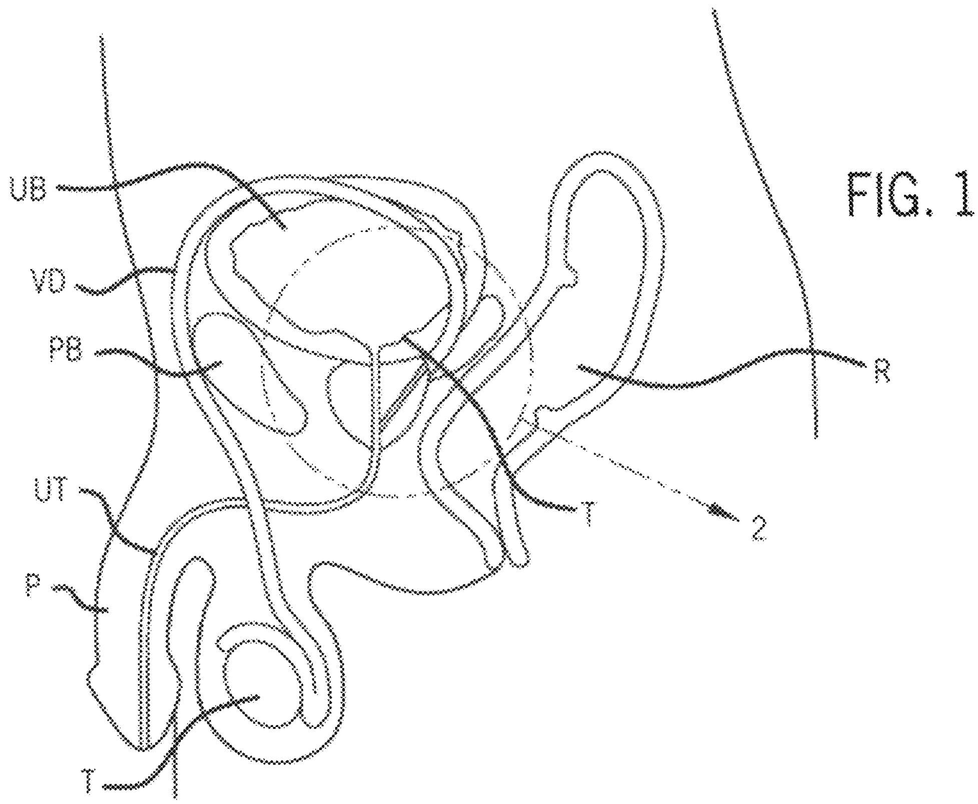
FIG. 1
FIG. 2
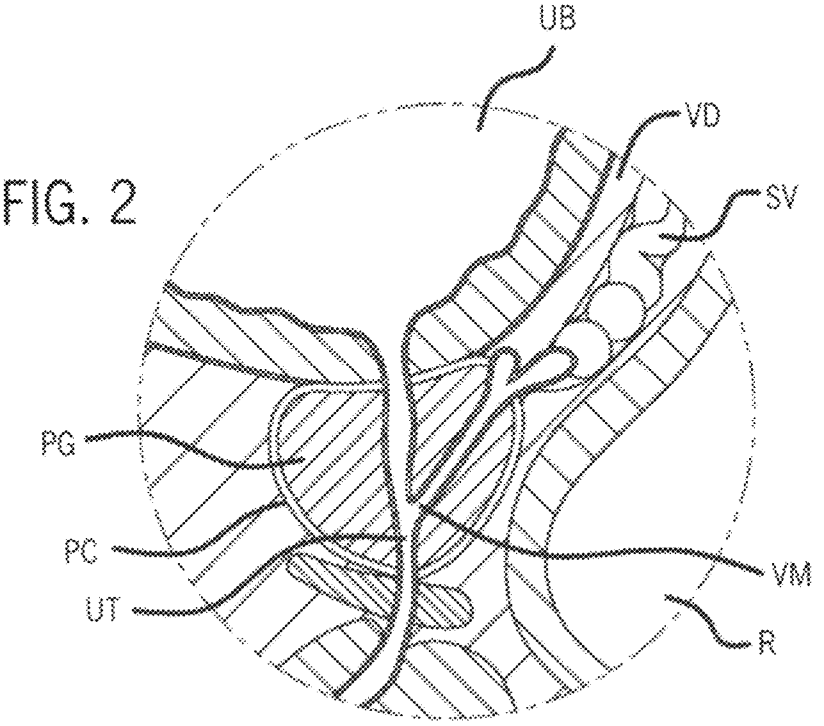

TISSUE-PIERCING IMPLANT

CROSS-REFERENCE TO RELATED APPLICATIONS

This application claims the benefit of priority to U.S. Provisional Appln. Ser. No. 63/568,753, filed Mar. 22, 2024, which is incorporated herein by reference in its entirety.

TECHNICAL FIELD

The subject matter of this patent document relates to the field of medical devices. More particularly, but not by way of limitation, the subject matter relates to medical devices, systems, and methods for relieving pressure on a prostatic urethra by compressing at least a portion of a prostate gland.

BACKGROUND

Benign Prostatic Hyperplasia (BPH) is one of the most common medical conditions that affect men, especially elderly men. It has been reported that, in the United States, more than half of all men have histopathologic evidence of BPH by age 60 and, by age 85, approximately 9 out of 10 men suffer from the condition. Moreover, the incidence and prevalence of BPH are expected to increase as the average age of the population in developed countries increases. Despite extensive efforts in both the medical device and pharmacotherapeutic fields, current treatments remain only partially effective and are burdened with significant side effects. Thus, there remains a need for the development of new devices, systems and methods for treating BPH as well as other conditions in which one tissue or anatomical structure impinges upon or compresses another tissue or anatomical structure.

SUMMARY

Embodiments disclosed herein include devices, systems, and methods for compressing at least a portion of a prostate gland to alleviate pressure on a prostatic urethra. Examples include a prostatic implant configured to anchor simultaneously to the outer prostatic capsule, and also a urethral side, of the lobe of an enlarged prostate, such as a median or lateral lobe. The implant may include a distal anchor portion comprising a distal piercing portion and a tail portion together configured to anchor on the outside of the prostatic capsule. An elongate middle portion, e.g., a suture, may connect the distal anchor portion to a proximal anchor portion or urethral endpiece configured to anchor to a urethral side of the lobe. In operation, once the distal anchor portion is implanted, the elongate middle portion may be tensioned and the proximal anchor portion subsequently attached thereto. Attachment of the proximal anchor portion may lock the tensioned middle portion in place such that the distal and proximal anchor portions are effectively urged toward each other, compressing the prostatic tissue therebetween and relieving constriction of the prostatic urethra.

The distal piercing portion of the implant may be configured to puncture the prostatic capsule during the implant delivery process, thereby eliminating the need for a separate piercing needle. In lieu of a piercing needle, an elongate needle or tubular push member having a distal end that is substantially blunt or flat, i.e., not beveled, pointed or tapered, may be used to deliver and unsheathe the implant.

Relative to preexisting prostatic anchoring devices, which typically feature a distal anchor member nestled within a piercing needle and positioned proximal to the needle's distal tip, the distance by which the distal anchor portion must be advanced beyond the prostatic capsule before anchoring may be advantageously reduced, as the distal anchor portion may require distal advancement only until its length is advanced beyond the capsule. The distal anchor portion itself may also be smaller, e.g., shorter, than preexisting implants, especially in embodiments featuring two tail portions, as further set forth below. The reduced size of the distal anchoring portion may contribute to the decrease in distal extension necessary for anchoring to the prostatic capsule. Omission of a piercing needle and decreased distal extension may reduce the likelihood of contacting bony structures distal to the prostatic capsule that may otherwise damage the delivery device or implant and prevent successful anchoring. In the event any bony structures are contacted, the cone shape of the distal anchoring portion, alone or in combination with its significant hardness, may prevent or reduce the extent of any damage incurred.

The implant has a tail portion operably connected to the distal piercing portion. The tail portion may include one or more distinct, pre-formed tail members or arms that may be biased so as to extend, curl, or spring away from a longitudinal axis of the tubular push member upon being released therefrom. For example, during the implant delivery process, at least a portion of the tail portion may be positioned within the tubular push member, proximal to the distal piercing portion. After the distal piercing portion pierces through the prostatic capsule and the tail portion is positioned just beyond the capsule's outer surface, the push member may be retracted proximally, unsheathing the tail portion outside the prostatic capsule. Unsheathing may also occur at least in part via distal advancement of the tail portion beyond the distal end of the push member. No longer bound within the inner lumen of the push member, the proximal tail portion may then curl, spring, or otherwise extend laterally or outwardly from the longitudinal axis of the tubular push member, expanding the footprint of the distal anchor portion, decreasing the amount of distal advancement necessary, and securely anchoring the distal portion of the implant to the capsular side of the lobe.

These and other examples and objects of the present devices, systems, and related methods will be set forth in the following Detailed Description. This Overview is intended to provide non-limiting examples of the present subject matter. The Detailed Description below is included to provide further information about the present devices, systems, and related methods. Neither is intended to provide an exclusive or exhaustive explanation of the present devices and methods because this disclosure is written for those of ordinary skill in the art.

BRIEF DESCRIPTION OF THE DRAWINGS

In the drawings, like numerals can be used to describe similar features and components throughout the several views. The drawings illustrate generally, by way of example but not by way of limitation, various embodiments discussed in the present patent document.

FIG. 1 illustrates a cross-sectional view of the anatomy surrounding a prostate in a human subject.

FIG. 2 illustrates an enlarged cross-sectional view of the anatomy surrounding a prostate.

Figure 3A:
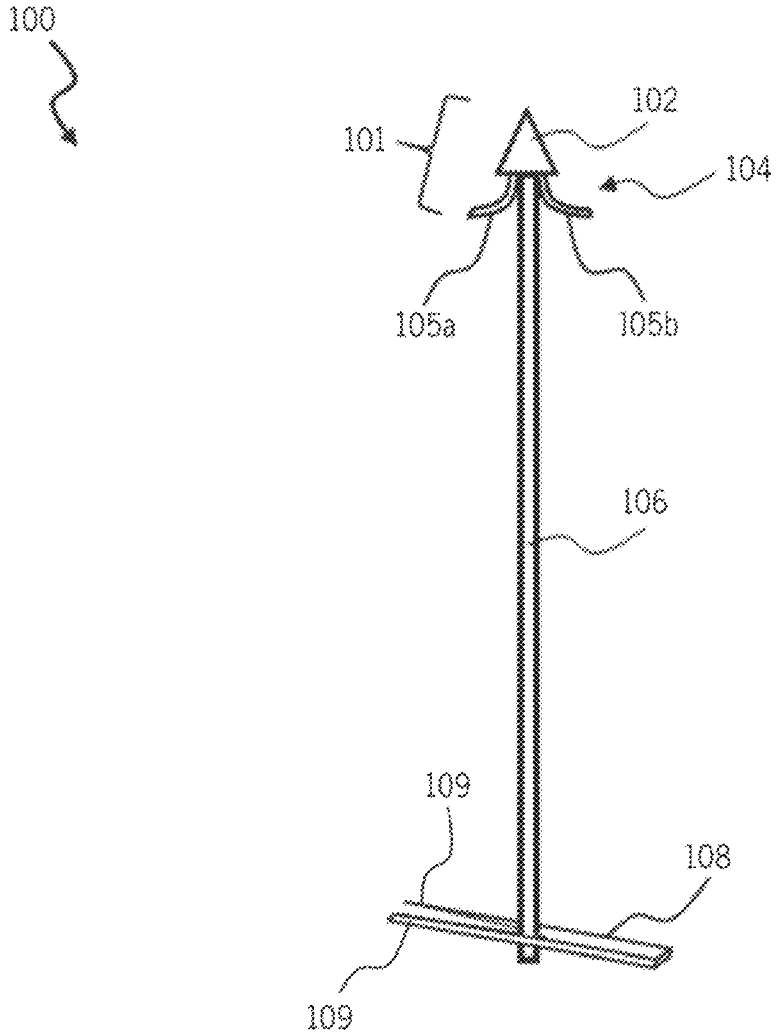
FIG. 3A illustrates an implant in accordance with embodiments of the present disclosure.

The drawing figures are not necessarily to scale. Certain features and components may be shown exaggerated in scale or in schematic form and some details may not be shown in the interest of clarity and conciseness.

DETAILED DESCRIPTION

The present devices and associated methods provide clinicians with a means to treat an enlarged prostate, which may be a symptom of benign prostatic hyperplasia, to alleviate its impingement on the adjacent prostatic urethra. Implants disclosed herein can be placed using a method for compressing a prostate gland or portion thereof according to the following description.

FIGS. 1 and 2 illustrate various features of the urological anatomy of a human subject. The prostate gland PG is a walnut-sized muscular gland located adjacent the urinary bladder UB. The urethra UT runs through the prostate gland PG. The prostate gland PG secretes fluid that protects and nourishes sperm. The prostate also contracts during sperm ejaculation to expel semen and provide a valve to keep urine out of the semen. A firm prostatic capsule PC surrounds the prostate gland PG.

The urinary bladder UB holds urine. The vas deferentia VD define ducts through which semen is carried, and the seminal vesicles SV secrete seminal fluid. The rectum R is the end segment of the large intestine through which waste is dispelled. The urethra UT carries both urine and semen out of the body. Thus, the urethra is connected to the urinary bladder UB and provides a passageway to the vas deferentia VD and seminal vesicles SV.

The trigone T is a smooth triangular end of the bladder. It is sensitive to expansion and signals the brain when the urinary bladder UB is full. The verumontanum VM is a crest in the wall of the urethra UT where the seminal ducts enter. The prostatic urethra is the section of the urethra UT that extends through the prostate.

FIG. 3A illustrates an embodiment of an implant 100 used to compress at least a portion of a prostate gland in a subject. The example shown includes a distal anchoring portion 101 comprising a distal piercing portion 102 and a tail portion 104 featuring tail members 105*a* and 105*b*. The implant 100 further includes a middle portion 106 and a proximal end, urethral endpiece, or anchoring portion 108. The middle portion 106 may comprise a suture that can be tightened or tensioned upon implantation, pulling the distal anchoring portion 101 tightly against the prostatic capsule and, after attachment of the proximal anchoring portion 108 to the middle portion 106, effectively biasing the distal and proximal anchoring portions toward each other and compressing the prostatic tissue therebetween. The implant 100 is shown in an unconstrained anchoring configuration, with the tail members 105*a*, 105*b* extended generally outwardly relative to the longitudinal axis of the middle portion 106 and the proximal anchoring portion 108 generally orthogonally oriented relative to the longitudinal axis of the middle portion 106. The unconstrained anchoring configuration may be the native, relaxed state of the device.

Figure 3B:
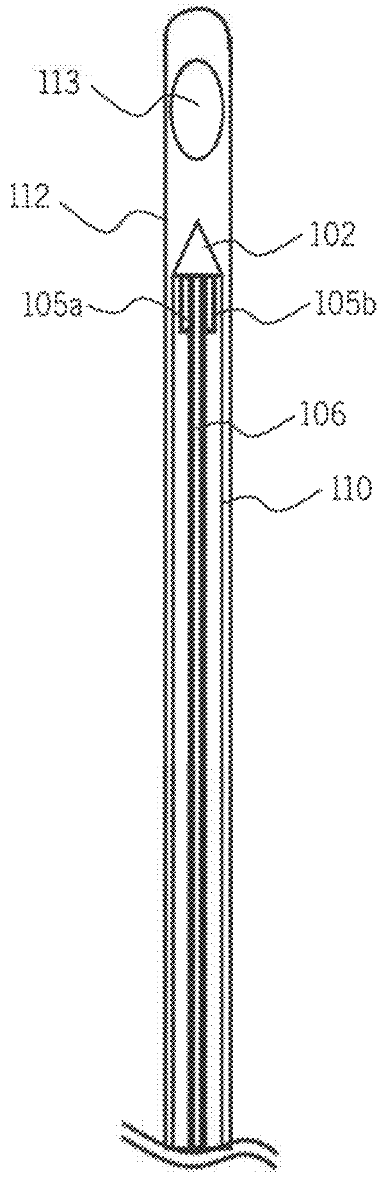
FIG. 3B illustrates the implant shown in FIG. 3A coupled with a tubular push member and elongate delivery device, both depicted in transparency.

FIG. 3B illustrates the implant 100 in a constrained delivery configuration, in which all but the distal piercing portion 102 is positioned within an elongate, tubular push member 110 defining an inner lumen. As shown, both tail members 105*a*, 105*b* are constrained within the inner lumen of the push member 110, such that the tail members 105*a*, 105*b* are substantially straight and oriented in the same general direction as the longitudinal axis of the push member 110. A tubular, elongate delivery member 112 surrounds the push member 110 and implant 100. The elongate delivery member 112 may be configured to navigate the urethra with the push member 110 and implant 100 housed therein, ultimately delivering both components to a targeted lobe of an enlarged prostate gland, where the push member 110 and implant 100 may exit the delivery member 112 through a sidewall opening 113 of the delivery member 112. The implant 100 may be positioned relative to the push member 110 in the manner shown until the distal anchoring portion 101 is advanced beyond the outer surface of the prostatic capsule, at which point the push member 110 may be retracted proximally while the implant 100 remains stationary.

While components of the assembly depicted in FIG. 3B appear substantially straight, various components may curve or bend to accommodate anatomical features during and after the delivery process. Accordingly, the shape, relative position, and/or angular orientation of one or more components shown in FIG. 3B should not be viewed as static or limiting.

The push member 110 may comprise a narrow, elongate tubular member with a blunt distal tip, with an end cut generally perpendicularly to the axis of the push member 110, configured to abut the proximal end of the distal piercing portion 102, such that the distal piercing portion 102 may be mounted on the distal end of the push member 110. Because the distal end of the push member 110 may abut the proximal end of the distal piercing portion 102 during implant delivery, a distal pushing force applied to the proximal end of the push member 110 may translate directly into distal movement of the implant 100. In some examples, the push member 110 may be structurally similar to a needle without an angled, beveled, or sharpened tip. Still further, the distal bevel of preexisting piercing needles may create challenges with gauging during passage of such needles through the distal tip of elongate delivery members. By contrast, the sharp distal tip positioned at the radial center of the distal end of the distal piercing portion 102 facilitates passage of the push member 110 and distal anchoring portion 101 through the elongate delivery member 112.

The pointed cone shape of the distal piercing portion 102 featured in various embodiments of the disclosed implant may also facilitate smooth coring through prostatic tissue, including the prostatic capsule. The solid, hard tip of the distal piercing portion 102 may also be resistant to damage in the event it contacts bony structures or hardened tissue, e.g., adenoma. Damage resistance may be especially pronounced relative to the hollow, beveled needles frequently utilized in preexisting devices, which may crimp or deflect upon contacting hard or stiff anatomical features, such as bones. Still further, because the distal piercing portion 102 is not confined within the lumen of a hollow needle during implant delivery, successful deployment of the disclosed implant may not be impeded in the event the distal piercing portion is damaged.

Components of the implant 100 may have different material compositions. For example, the material composition of the tail members 105*a*, 105*b* may be substantially flexible or elastic to enable the outward spring action of the tail members 105*a*, 105*b* upon their release from the push member 110. Non-limiting example materials constituting the tail members 105*a*, 105*b* include a flexible stainless steel, a shape memory Nitinol, one or more metals or alloys, and/or a polymer of suitable elasticity. In one embodiment, the distal piercing portion 102 and tail members 105*a*, 105*b* are formed from a single monolithic material. In another embodiment, the distal piercing portion 102 and tail member 105*a*, 105*b* are made from two or more separate materials secured together.

Embodiments of the middle portion 106 may include a suture comprising a polyester or monofilament, e.g., Poly Ethylene Terephthalate (PET). Non-limiting examples may include a suture comprised of a round monofilament extrusion/pulltrusion, which may be composed of a grade 8816 polyethylene terephthalate. In embodiments featuring a suture, the base material may be annealed at approximately 100 degrees Celsius for approximately 130 minutes in a straight condition. In one embodiment, the middle portion 106 may comprise a PET suture having a diameter of 0.015 inches and a tensile strength greater than or equal to about 12.7 pounds. Other suitable materials and dimensions also may be used.

The distal piercing portion 102 and/or proximal anchoring portion 108 may comprise stainless steel and/or a nickel titanium alloy, e.g., an electro-polished Nitinol. In one embodiment, the proximal anchoring portion 108 may be a 316L stainless steel flattened tube that is slotted, electro-polished, and passivated.

Embodiments of the proximal anchoring portion 108 may include a variety of modified, additional, or substitute components, compositions, features, and/or configurations, such as those of the anchor 84 described in U.S. Pat. No. 9,034,001, the entire contents of which are incorporated by reference herein. As shown in FIG. 3A, for instance, one non-limiting example of the proximal anchoring portion 108 may comprise a slotted, flattened-tubular member defining two prongs 109 that may grip and deform the middle portion 106. Additional proximal anchors or proximal end portions may comprise different components that couple with the middle portion 106, tubular push member 110, and/or elongate delivery member 112 in a different manner. Additional configurations of the proximal anchoring portion 108 may also anchor and/or secure the implant 100 to the urethral side of a lobe of a prostate gland by a variety of mechanisms. The configuration of the proximal anchoring portion 108 and its attachment to the implant 100 and/or lobe may thus vary.

The distal piercing portion 102 may have a shape and material composition that are less susceptible to being damaged during delivery. For instance, the cone shape featured in embodiments of the distal piercing portion 102 may be less likely to incur damage during delivery, for example when hard or firm anatomical features are encountered during distal advancement through and beyond a targeted lobe. Non-limiting examples of such anatomical features may include rigid bony surfaces, tissue regions having elevated density or firmness (e.g., tumors), and other irregular features that may impede smooth penetration into and through a targeted lobe. The material composition of the distal piercing portion 102 may also be harder and sturdier than a traditional pointed or beveled distal end of a piercing needle, further enhancing its resistance to damage. Relatedly, because the distal piercing portion 102 is not contained within and proximal to the distal end of a piercing needle, damage to the distal piercing portion 102 may not prevent its successful delivery and the subsequent unsheathing of the remainder of the implant 100. By contrast, a traditional piercing needle may crimp, break, or become bent in a manner that prevents unsheathing and ultimate deployment of a distal anchoring feature carried within the needle.

Embodiments of the implant 100 may also feature one or more markers used to determine whether insertion of the implant 100 is complete. For instance, one or more portions or components of the distal anchoring portion 101, e.g., the distal piercing portion 102 and/or the tail member(s) 105*a*, 105*b* may feature a radiopaque marker visible only after reaching the outer surface of the prostatic capsule PC. Detection of the marker either in real time during a procedure or after implantation is complete, indicates that the distal anchoring portion 101 has been sufficiently advanced and the capsular anchor formed properly. If performed during a procedure, marker detection may be achieved via fluoroscopy to confirm whether the distal anchoring portion 101 is fully advanced beyond the prostatic capsule, where the capsular anchor can form via lateral extension of the tail portion 104 on the outer surface of the prostatic capsule. If fluoroscopic detection of the marker shows that the distal anchoring portion 101 is not yet positioned fully outside the prostatic capsule, distal advancement of the push member 110 may continue until it is.

Figure 4A:
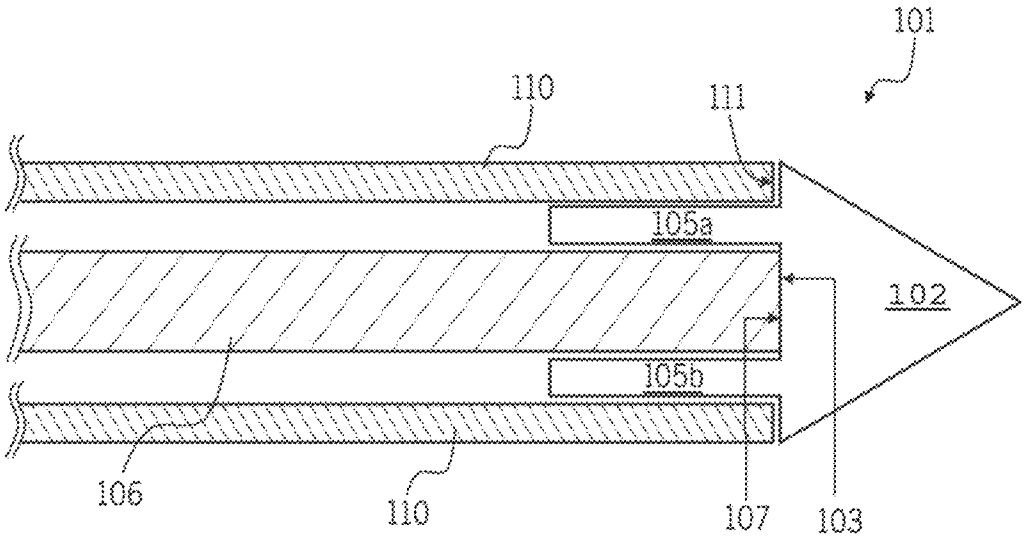
FIG. 4A illustrates a cross-sectional side view of a distal portion of an implant partially enclosed within a tubular push member in accordance with embodiments of the present disclosure.

FIG. 4A is a cross-sectional side view of the distal anchoring portion 101 of the implant 100 in a constrained delivery configuration, showing a distal portion of the push member 110 and the middle portion 106. As shown, the distal piercing portion 102 may define a sharp, pointed tip configured to pierce tissue, including tough prostatic capsular tissue. The distal end 107 of the middle portion 106 may be bonded, fixed, or otherwise secured to the proximal end 103 of the distal piercing portion 102. The distal end 111 of the push member 110 may abut the outer portions of the proximal end 103 of the distal piercing portion 102. To avoid snagging tissue (including the urethral wall and prostatic capsule) during its distal advancement therethrough, the cross-sectional diameter of the tubular push member may be approximately equal to, or less than, the cross-sectional diameter of the proximal end 103 of the distal piercing portion 102. The tubular push member 110 may, in various examples, have a cross-sectional diameter that is less than the maximal cross-sectional diameter of the proximal end 103 of the distal piercing portion 102.

The tail members 105*a*, 105*b* extend proximally from the proximal end 103 of the distal piercing portion 102, between the inner surface of the push member 111 and the outer surface of the middle portion 106. The tail members 105*a*, 105*b* may be positioned between the push member 110 and middle portion 106 in a manner that allows the push member 110 to slidably retract relative to the tail members 105*a*, 105*b* without sticking or catching. In some examples, one or more small lateral gaps may exist between the push member 110, tail members 105*a*, 105*b* and/or the middle portion 106 when the assembly is in the constrained delivery state. Additional examples may not include gaps between the components. According to such examples, the material compositions of the push member 110 and tail members 105*a*, 105*b* may facilitate relative sliding between the components. Some examples, for instance, may feature a smooth coating on the inner surface of the push member 110 and/or outer surface of the tail members 105*a*, 105*b*.

In some embodiments, the tail members 105*a*, 105*b* may not be formed integrally with the distal piercing portion 102. As noted above, the tail members 105*a*, 105*b* may have a different material composition than the distal piercing portion 102. The tail members 105*a*, 105*b* may be substantially elastic and pre-formed to spring outwardly upon retraction of the push member 110, whereas the distal piercing portion 102 may be substantially hard and rigid to facilitate piercing through tissue without being damaged. Like the middle portion 106, the tail members 105*a*, 105*b* may thus be bonded, fixed, or otherwise secured to the proximal end 103 of the distal piercing portion 102.

Alternatively, the tail members 105*a*, 105*b* and distal piercing portion 102 may be formed integrally and comprised of the same or substantially same materials. According to such embodiments, the tail members 105*a*, 105*b* may be pre-formed to bias outwardly, away from the longitudinal axis of the push member's distal end 111, whereas the distal piercing portion 102 may not be pre-formed or otherwise biased, such that its size and shape remains unchanged during and after implantation.

Figure 4B:
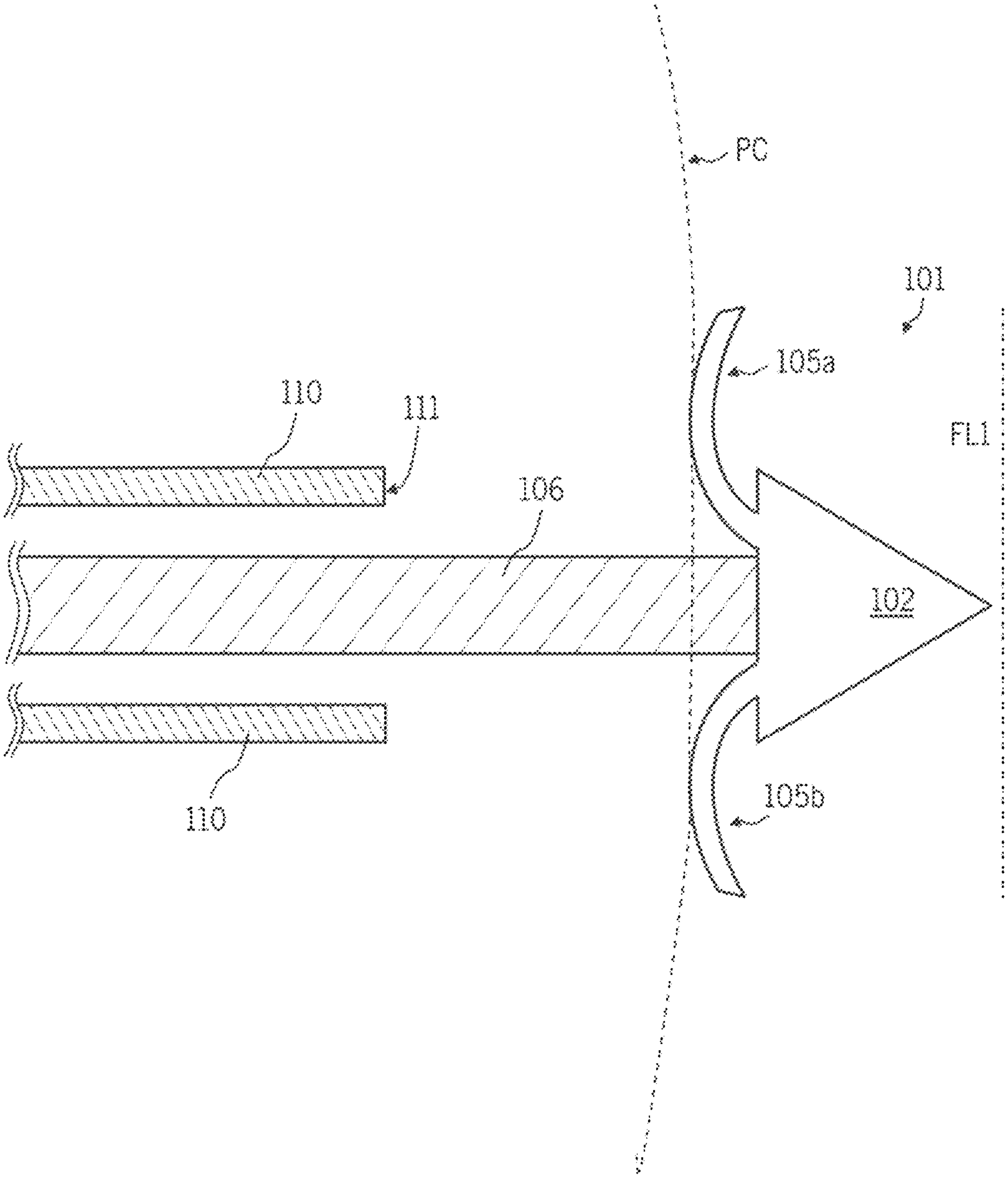
FIG. 4B illustrates a cross-sectional side view of the distal portion of the implant shown in FIG. 4A after proximal retraction of the tubular push member.

FIG. 4B is a cross-sectional side view of the distal anchoring portion 101 of implant 100, including a distal portion of the push member 110 and the middle portion 106, after advancement of the distal piercing portion 102 and the tail members 105*a*,*b* across the prostatic capsule PC and after partial retraction of the push member 110 and the distal anchoring portion 101. The distal anchoring portion 101 has assumed its anchoring configuration, in which the tail members 105*a*, 105*b* have extended outwardly, away from the longitudinal axis of the distal portion of the push member 110. The footprint length FL1 of the distal anchoring portion 101 may equal the distance from the distal tip of tail member 105*a* to the distal tip of tail member 105*b*, approximately perpendicular to the longitudinal axis of the distal portion of the push member 110. Because the footprint length FL1 is equal to the combined lengths of tail members 105*a* and 105*b*, the need for a single anchoring feature similar or equivalent to a tail member and having a footprint length equal to or greater than FL1 may be eliminated. As a result, the distance by which the implant must be advanced distally before the distal anchoring portion 101 is positioned beyond the prostatic capsule PC may be reduced.

The released tail members 105*a*, 105*b* curve to a predetermined radius of curvature in the example shown, but the particular shape of the tail members in the unconstrained anchoring configuration may vary. Additional embodiments may feature tail members 105*a*, 105*b* that spring outwardly but remain straight, for example, such that the tail members form acute angles with the middle portion 106 after their release from the push member 110. The degree of curvature and/or outward extension may vary, such that tail members pre-formed to curve may form arcs of different lengths.

Upon securing the distal anchoring portion 101 to the prostatic capsule and tensioning the middle portion 106, the tail members 105*a*, 105*b* may be pulled against the outer surface of the prostatic capsule PC, such that the tail members 105*a*, 105*b* substantially conform to, or deflect against, the surface of the prostatic capsule PC.

Figure 5A:
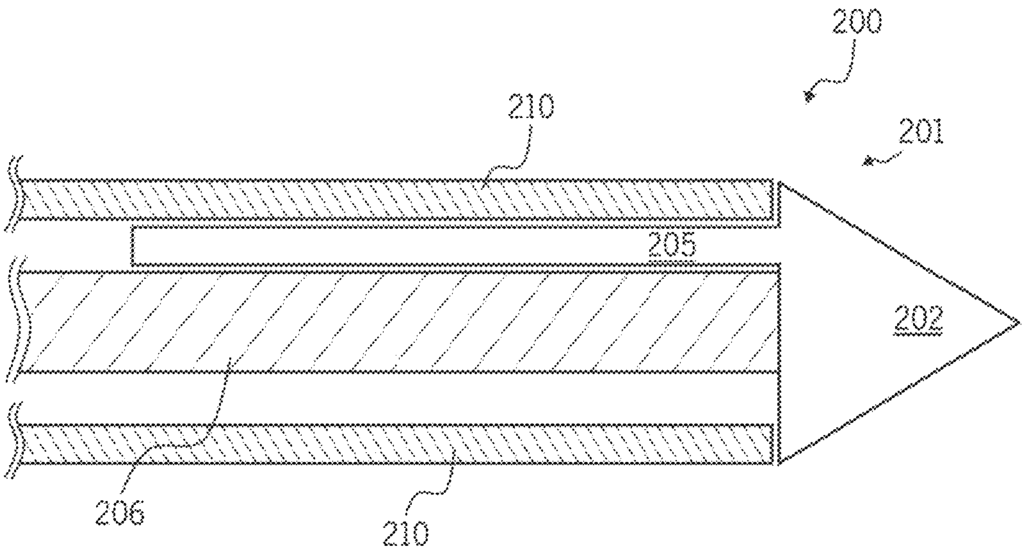
FIG. 5A illustrates a cross-sectional side view of a distal portion of another implant partially enclosed within a tubular push member in accordance with embodiments of the present disclosure.
Figure 5B:
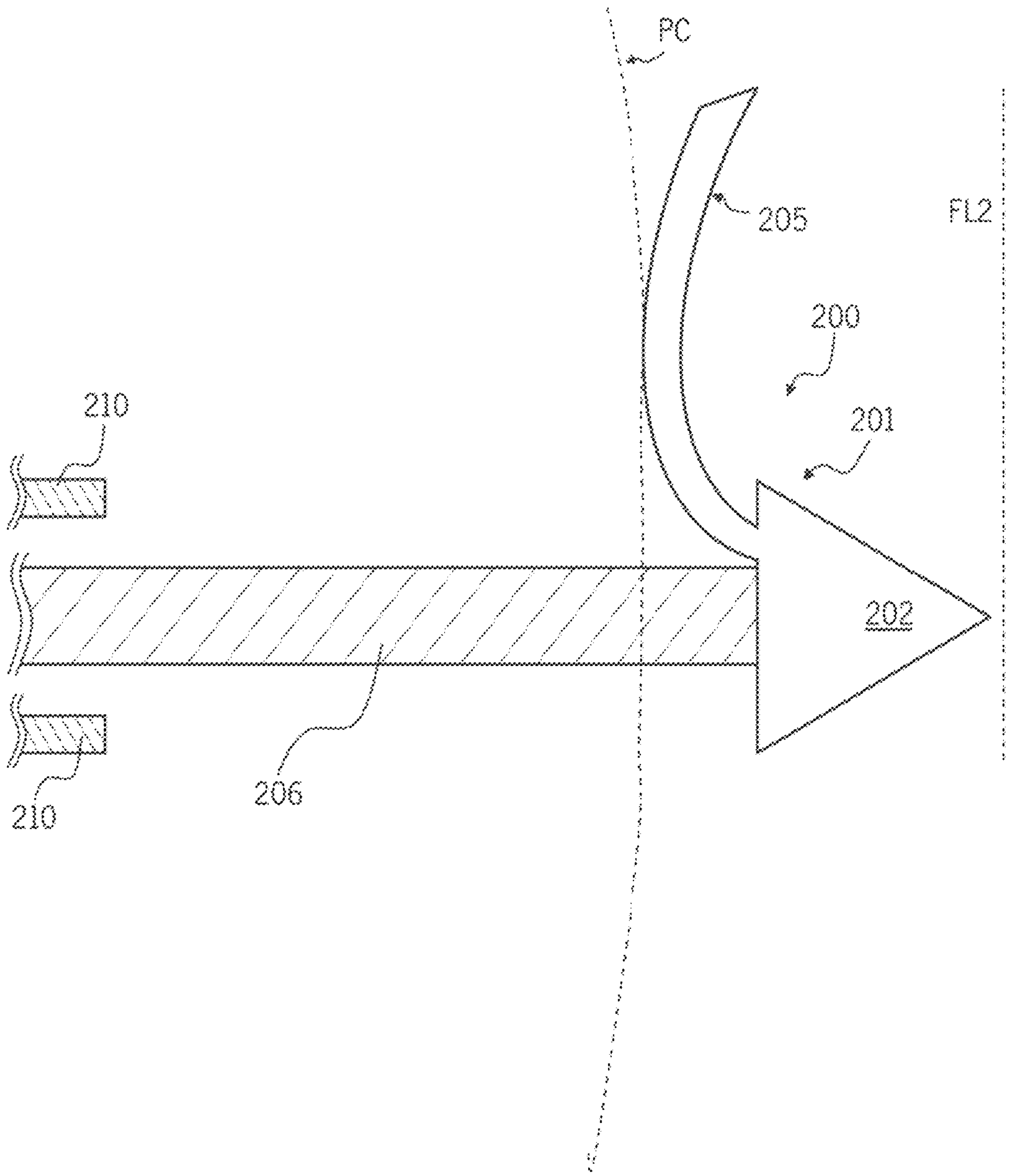
FIG. 5B illustrates a cross-sectional side view of the distal portion of the implant shown in FIG. 5A after proximal retraction of the tubular push member.

FIG. 5A is a cross-sectional side view of a distal anchoring portion 201 of an implant 200 featuring a single tail member 205 extending proximally from a distal piercing portion 202. The distal anchoring portion 201 is depicted in a constrained delivery configuration in which the tail member 205 and middle portion 206 are housed within a distal portion of a push member 210. In an embodiment, tail member 205 may be longer than the tail members 105*a*, 105*b* of implant 100, such that the longer length configures the tail member 205 to extend a greater distance from the middle portion 206 upon retraction of push member 210. This may expand the anchoring footprint of tail member 205 to a size that may be comparable to the combined footprint of tail members 105*a*, 105*b*. FIG. 5B illustrates the distal anchoring portion 201 of implant 200 after retraction of the push member 210 to a position proximal to the proximal end of tail member 205. The distal anchoring portion 201 has assumed its unconstrained anchoring configuration, in which the tail member 205 has sprung outwardly, away from the longitudinal axis of the push member 210. The footprint length FL2 of distal anchoring portion 201 may be approximately equal to the footprint length FL1 of distal anchoring portion 101. Additional embodiments may feature a distal anchoring portion 201 having a footprint length that is shorter or longer than the footprint length of distal anchoring portion 101.

Upon securing the distal anchoring portion 201 of the implant 200 to the prostatic capsule PC of the lobe and tensioning the middle portion 206, the tail member 205 may be tightly secured against the outer surface of the prostatic capsule PC, such that the tail member 205 substantially conforms to, or is deflected against, the surface of the prostatic capsule PC.

In addition to length and curvature, the shape of each tail member may vary. Embodiments may feature flaps, prongs, or broader, fan-like tail members. Tail members may also resemble a plurality of spokes or a single parachute-like body configured to expand over the outer surface of the prostatic capsule upon proximal retraction of a corresponding push member. The number of tail members may vary, from zero, to one, two, or more.

The prostatic implants disclosed herein may be delivered to a targeted prostate gland using a delivery system that further includes a delivery device comprising a tubular elongate member, e.g., elongate delivery member 112. Examples of the delivery device may generally include a handle assembly supporting an elongate portion comprising a tubular elongate member, such as a sheath. The elongate member defines a low profile suited to navigate body anatomy to reach an interventional site. Substructure may be provided to maintain a longitudinal profile of the elongate member so that the interventional procedure can progress as intended. The elongate member may be substantially rigid, such that it maintains an approximately straight configuration, or it may be substantially flexible and/or steerable, such that it may conform to the curved anatomy of a subject. Embodiments of the delivery device may also include an endoscope, providing the ability to view the interventional procedure. Using the disclosed systems, insertion of one or more implants in a prostate gland may be performed in an outpatient setting.

Figure 6:
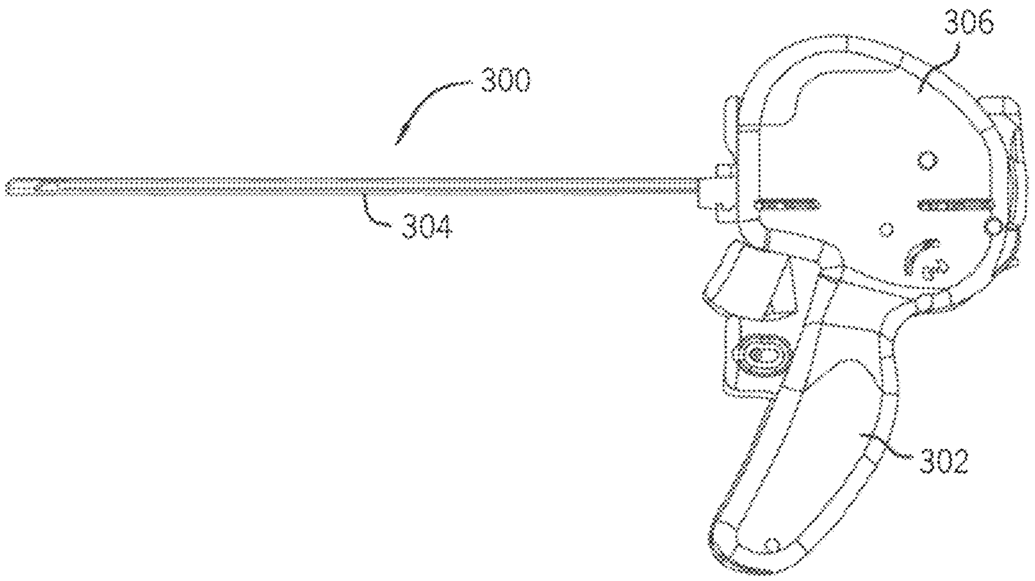
FIG. 6 illustrates a side view of a delivery device for an implant in accordance with embodiments of the present disclosure.

FIG. 6 illustrates one example of a delivery device 300 having structure configured to gain access to an interventional site and deploy a prostatic implant, such as implant 100. As shown, the delivery device 300 may include a handle assembly 302 connected to a tubular, elongate delivery member 304 (e.g., elongate delivery member 112). The elongate delivery member 304 may be sized to fit within a cystoscopic sheath for patient tolerance during a procedure in which the subject is awake rather than under general anesthesia. A non-limiting example of the cystoscopic sheath may be a 19 F sheath, which may also be substantially elastic or flexible.

The delivery device 300 may further include a number of subassemblies configured to deliver and employ an implant at a target site. A handle case assembly 306, including handle components that form part of the handle assembly 302, may be included. The handle assembly 302 is sized and shaped to fit comfortably within an operator's hand and can be formed from conventional materials. Windows can be formed in the handle case assembly 306 to provide access to internal mechanisms of the device so that a manual override is available to the operator in the event the interventional procedure needs to be abandoned.

The elongate delivery member 304 defines an inner lumen sized and configured to accommodate longitudinal insertion of at least a hollow push member and prostatic implant therethrough. Non-limiting embodiments of the elongate delivery member 304 may include a 19 Fr or 21 Fr sheath or any other suitable size. The elongate delivery member 304 may have a shape and/or flexibility that configures it to navigate through a urethra without kinking or puncturing the urethral wall. In some examples, the elongate delivery member 304 may be substantially rigid, such that it maintains an approximately straight configuration during its insertion through the urethra. According to such examples, the distal portion of the elongate delivery member 304 may be angled toward or away from various anatomical features surrounding the urethra, e.g., one or more lobes of the prostate gland, by adjusting the angular orientation of the proximal end of the elongate delivery member 304 outside the body. The distal end of the elongate delivery member 304 may comprise smooth, blunt, and/or beveled surfaces to avoid puncturing the urethral wall, especially upon adjusting its angular orientation after insertion.

Embodiments of the delivery device may include a variety of additional or substitute components and subassemblies, such as those described in U.S. Pat. No. 10,130,353, the entire contents of which are incorporated by reference herein.

Prior to insertion of any components of the delivery system, the implant recipient may undergo a regimen of antibiotics. Local anesthesia can be employed for the interventional procedure. A combination of an oral analgesic with a sedative or hypnotic component can be ingested by the subject. A topical anesthesia such as lidocaine liquids or gel can be applied to the bladder and urethra.

Examples of the implantation process may generally involve advancing the distal end of a tubular elongate member containing a coaxial push member through the urethra of a subject until the distal end reaches the prostatic urethra, adjacent one or more lobes of the enlarged prostate gland targeted for compression. All but the distal piercing portion of a prostatic implant (e.g., implant 100) is positioned within the push member in a constrained delivery configuration. The push member is then advanced through and beyond a distal portion of the elongate member, led by the distal piercing portion of the implant, which subsequently pierces through the urethral wall, targeted prostatic lobe, and prostatic capsule.

The push member may then be retracted proximally toward the urethra, where the elongate member remains. As the push member is retracted, the prostatic implant is unsheathed in a distal-to-proximal direction, such that the distal anchoring portion of the implant is unsheathed first, outside the prostatic capsule. No longer bound within the inner lumen of the push member, the tail portion of the implant assumes its unconstrained configuration with the tail member(s) extended outwardly, anchoring the implant to the capsular side of the lobe. The middle portion of the implant is then unsheathed within the lobe. After the distal end of the push member is further retracted back into the urethra and elongate member, the middle portion may be tensioned such that the distal anchoring portion is pulled tightly against the prostatic capsule. The proximal anchoring portion of the implant may then be secured to the tensioned middle portion on the urethral side of the lobe, where it may assume a generally orthogonal orientation with respect to the middle portion. With the implant fully deployed, the elongate member containing the push member may then be retracted proximally through the urethra until exiting the subject.

Figure 7A:
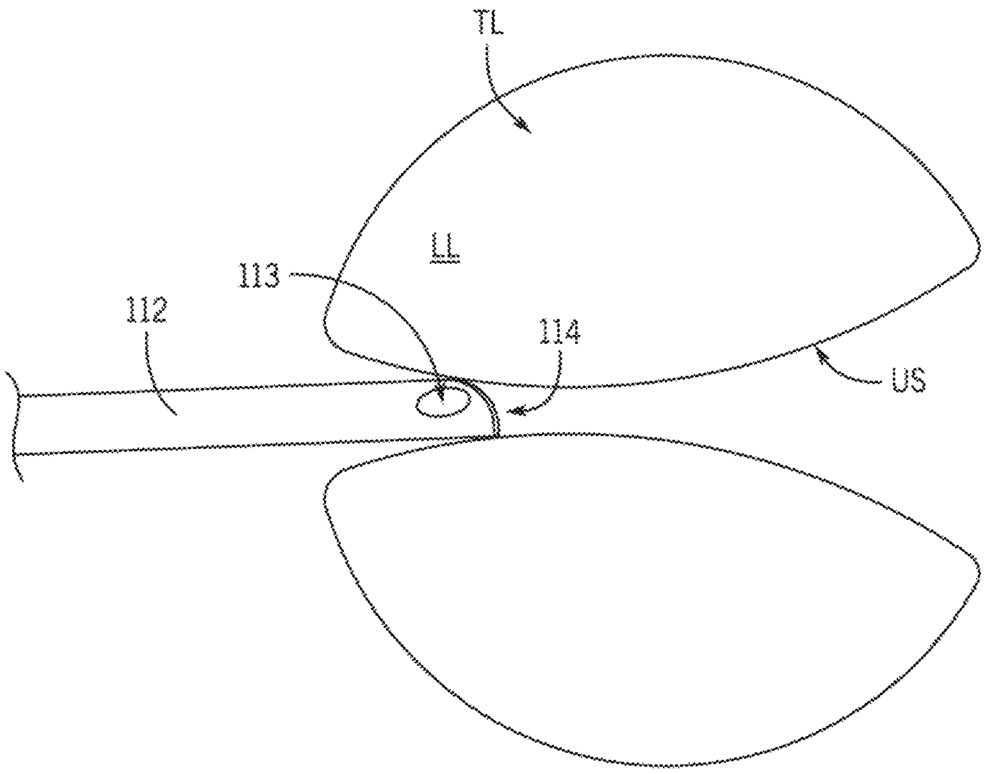
FIG. 7A illustrates a depiction of a step performed during an implantation procedure in accordance with embodiments of the present disclosure.

FIG. 7A illustrates a step in an example procedure for deploying a prostatic implant in a lateral lobe of a subject in accordance with embodiments disclosed herein. Implant 100 is depicted and referenced for ease of illustration.

After preparing the treatment site for the procedure, the distal end 114 of the elongate delivery member 112 may be inserted into the urethra (directly or within a pre-placed introducer sheath) and advanced distally therethrough, toward the urinary bladder, until it reaches the prostatic urethra, between lateral lobes LL of the prostate gland, at least one of which may be an enlarged targeted lobe TL. In some examples, the targeted lobe TL of the prostate gland is chosen while the device extends through at least a portion of the prostatic urethra. In other embodiments, the targeted lobe TL is identified prior to the procedure, for example via ultrasound imaging. A distal portion of the elongate delivery member 112 may, in some examples, be advanced into the bladder, where it may be positioned and/or rotated as needed to deploy the implant as desired within the targeted lobe TL upon retracting the elongate delivery member 112 until its distal end 114 returns to the prostatic urethra.

Figure 7B:
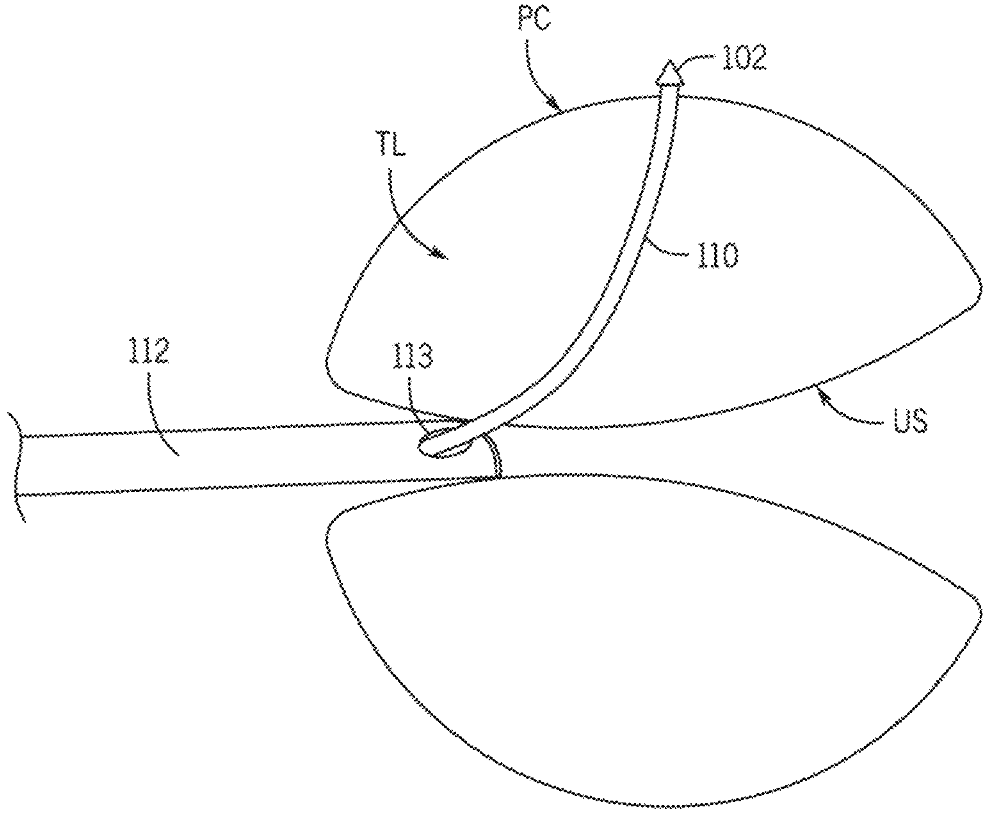
FIG. 7B illustrates a depiction of another step performed during an implantation procedure in accordance with embodiments of the present disclosure.

As shown in FIG. 7B, the push member 110 may be advanced distally and laterally through a sidewall opening 113 defined near the distal end 114 of the elongate delivery member 112, led by the distal piercing portion 102 of the implant 100, such that the push member 110 may curve and extend substantially orthogonally or perpendicularly away from the longitudinal axis of the elongate delivery member 112, for example in the manner shown and described in U.S. Pat. No. 11,298,115, the entire contents of which are incorporated by reference herein. Additional embodiments may involve advancing the push member 110 through an opening defined by the distal end 114 of the elongate delivery member 112. Such embodiments may or may not define a sidewall opening. The clinician continues to advance the push member 110 distally until the distal piercing portion

102 pierces the urethral side of the targeted lobe TL, passes through the prostatic tissue, and ultimately pierces the prostatic capsule PC.

Figure 7C:
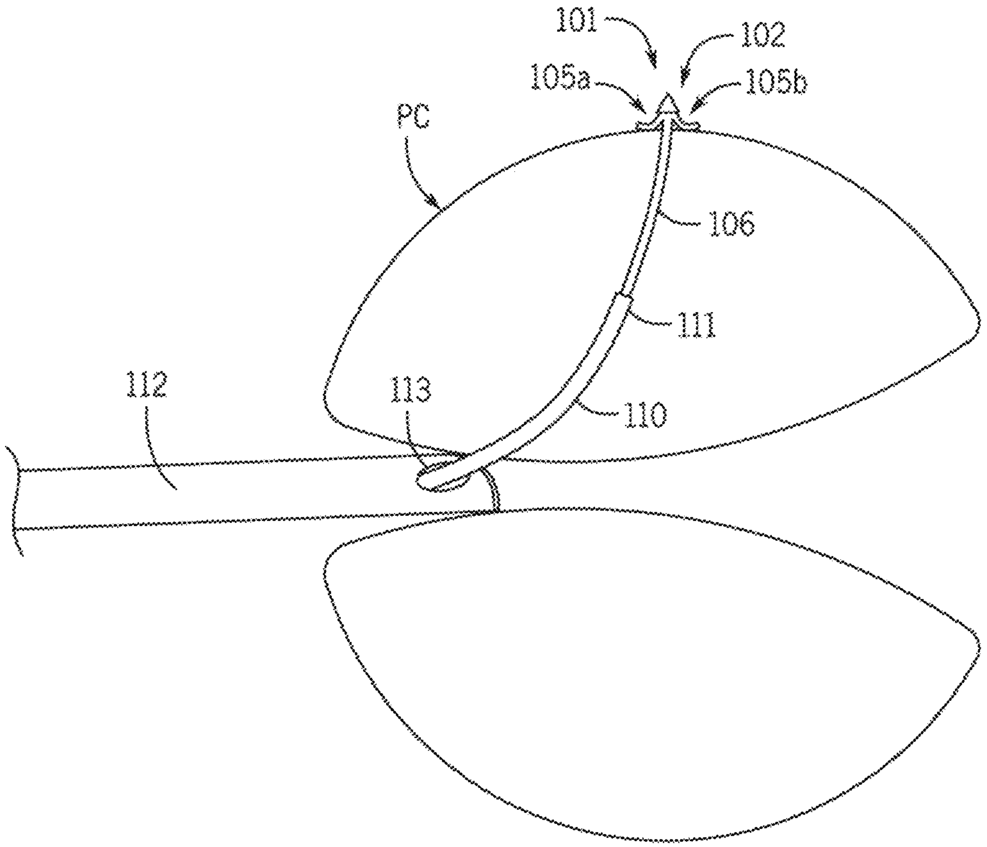
FIG. 7C illustrates a depiction of another step performed during an implantation procedure in accordance with embodiments of the present disclosure.

After at least the distal piercing portion 102 and tail portion extend beyond the prostatic capsule PC, the push member 110 may be retracted proximally while the implant positioned therein is not retracted, as shown in FIG. 7C, resulting in the push member 110 unsheathing the implant 100 in a distal-to-proximal direction, starting with the distal piercing portion 102 and the tail members 105*a*, 105*b* of the implant 100, which are unsheathed outside the prostatic capsule PC. Free from the constraints of the push member 110, the tail members 105*a*, 105*b* may expand or spring outwardly over the surface of the prostatic capsule PC. Continued retraction of the push member 110 unsheathes the middle portion 106 of the implant 100 within the targeted lobe TL. The push member 110 is further retracted until its distal tip 111 is retracted through the urethral side US and back into the elongate delivery member 112, as shown in FIG. 7D.

Once the push member 110 is fully retracted from the targeted lobe TL, tension may be applied to the middle portion 106, pulling the distal anchoring portion 101 tightly against the prostatic capsule. The proximal anchoring portion 108 of the implant may then be attached to the proximal end of the tensioned middle portion 106, and the surplus middle portion severed proximal to the secured proximal anchoring portion 108. In other embodiments, the middle portion 106 may be tensioned after its attachment to the proximal anchoring portion 108, which may result in the proximal anchoring portion 108 being pulled tightly against the urethral side US in a manner resembling a zip-tie or ratchet mechanism, for example.

Figure 7D:
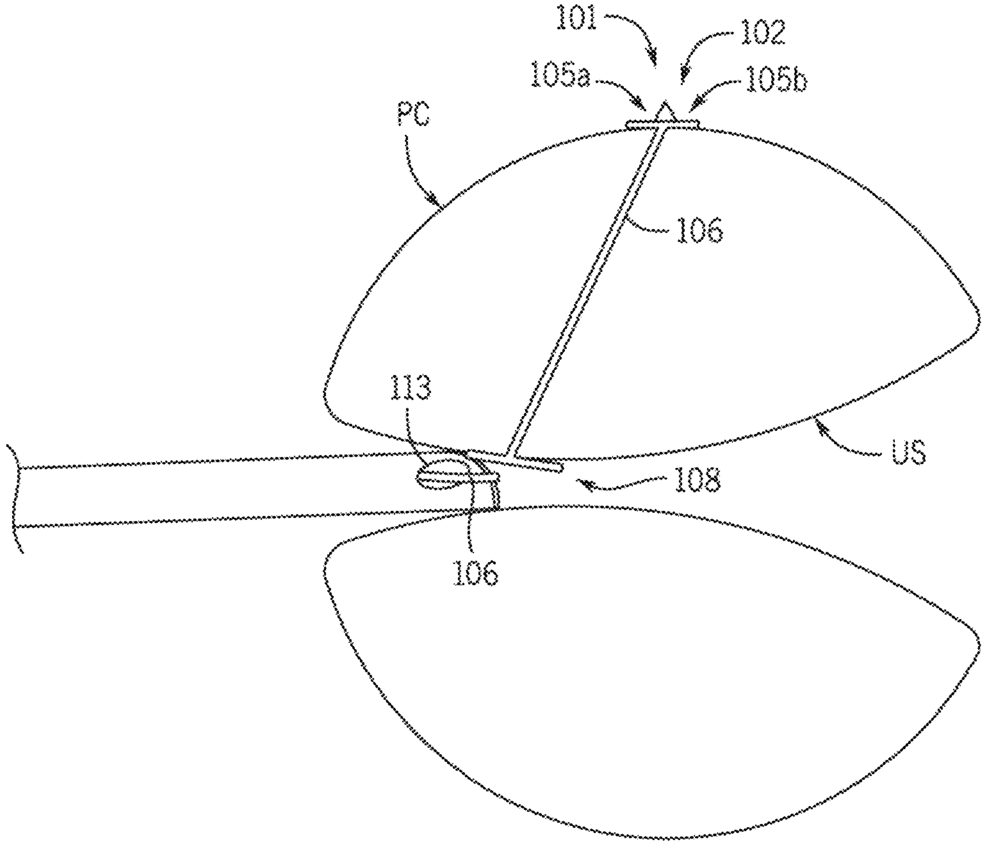
FIG. 7D illustrates a depiction of another step performed during an implantation procedure in accordance with embodiments of the present disclosure.

The push member 110 may be retracted into the elongate delivery member 112, for example before tensioning the middle portion, and the two components retracted proximally together through the urethra, leaving the implant 100 at the targeted lobe TL As further shown in FIG. 7D, the tail members 105*a*, 105*b* of the distal anchoring portion 101 may be tightened against the outer surface of the prostatic capsule PC upon tensioning the middle portion 106. As a result, the tail members 105*a*, 105*b* may substantially conform to, or deflect against, the surface of the prostatic capsule PC and form a capsular anchor configured to resist or prevent proximal movement of the implant 100. The surface of the prostatic capsule PC may not be uniformly flat or planar, however, such that the tail members 105*a*, 105*b* may not be perfectly or even substantially parallel to or flush with the prostatic capsule PC. The relative orientation between the distal anchoring portion 101 and the prostatic capsule PC may thus depend on the surface features of the capsule.

Because the distal piercing portion 102 leads the implant 100 through the lobe and pierces the prostatic capsule, unsheathing of the implant 100 may occur sooner and/or more quickly relative to preexisting capsular anchors in which the implant resides substantially proximal to the tip of the needle bevel before deployment. In accordance with preexisting anchor deployment procedures, the tip of the distal anchoring portion of a prostatic implant resides well proximal of the piercing needle housing the implant during delivery. As a result, during unsheathing the needle has to retract a number of millimeters before the distal anchor can begin to unsheathe. The piercing needle thus has to be positioned farther outside the capsule to ensure the anchor fully unsheathes distal to the capsule. With implant 100, the distance the distal piercing portion 102 needs to extend beyond the capsule to ensure the distal anchoring portion 101 unsheathes entirely outside the capsule may be significantly shorter. This may reduce the likelihood of the anchoring portion 101 failing to fully deploy outside the prostatic capsule, which would likely result in the implant pulling through the lobe after implantation. Such pull-through events may cut or tear the prostate gland and diminish its intended compression. The shorter distance that the piercing portion 101 must unsheathe also reduces the risk of striking bone or other undesired tissues or organs.

Implants having different configurations and properties may be used for different cases. For instance, an implant of having a greater number of tail members may be used to compress an enlarged prostate gland of relatively high stiffness or size. Similarly, tail members having wider or greater surface areas, such as tail members having fanned or winged shapes, may be used to compress more enlarged prostate glands, whereas smaller glands may be compressed using implants having more narrow tail members having a smaller collective footprint. The length of each tail member may also vary for different anatomies. For instance, longer tail members may be used to expand the footprint on more enlarged and/or stiffer prostate glands. Additional properties of an implant may be adjusted to match the properties of an enlarged prostate gland. Accordingly, methods of treating enlarged prostate glands may also involve determining one or more properties of an enlarged prostate gland, such as size and/or stiffness, and selecting an implant based on the properties. Other embodiments may feature a "one-size-fits-all" implant configured to accommodate any or most prostate glands.

In some cases, implant selection may also involve determining the number of implants to employ, with more implants typically required for more enlarged prostate glands.

Figure 8:
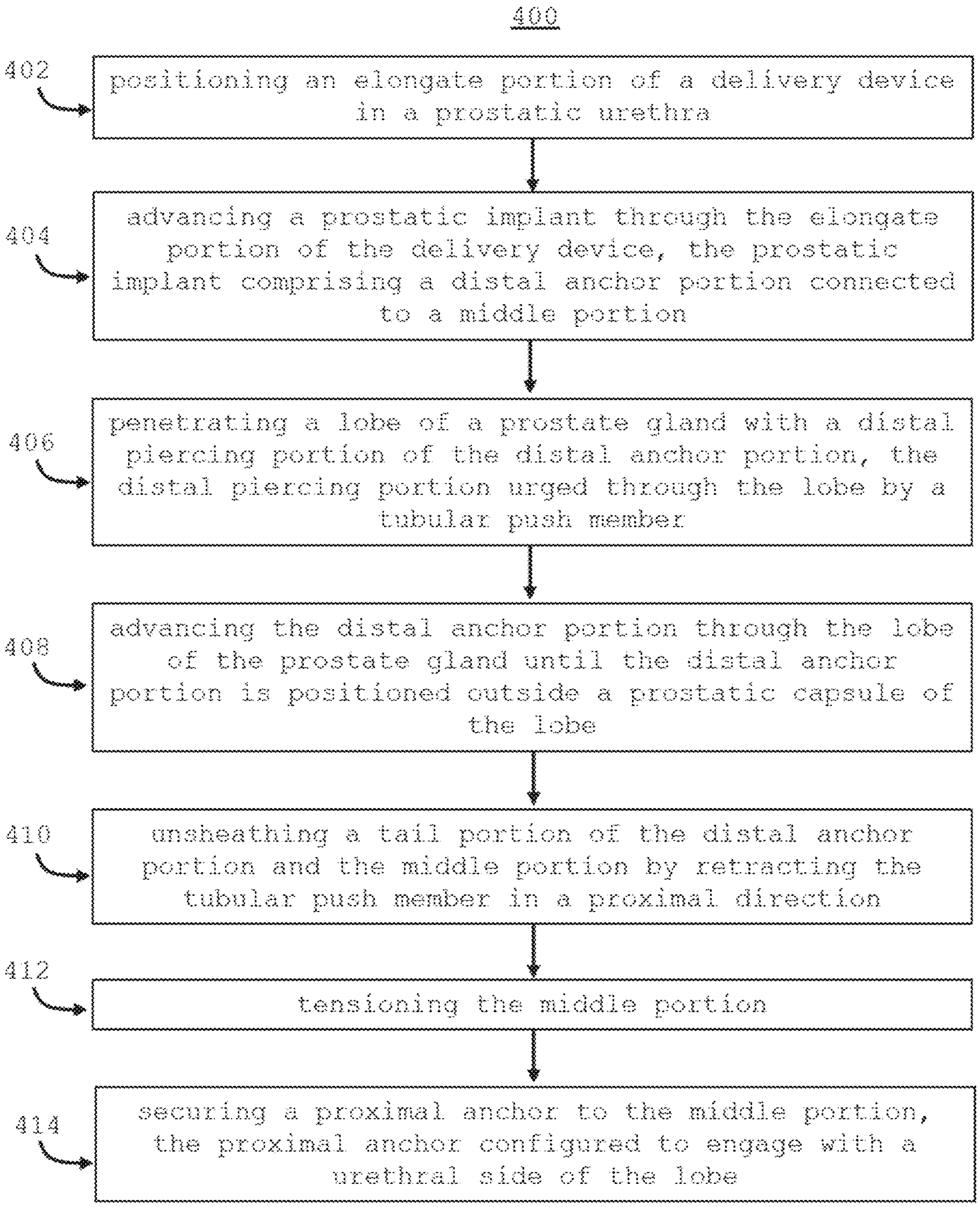
FIG. 8 illustrates a flow diagram of a method of delivering an implant to a prostate in accordance with embodiments of the present disclosure.

FIG. 8 is a flow diagram of a non-limiting example of a method 400 of delivering an implant to a prostate gland in accordance with embodiments of the present disclosure. The example method 400 may be performed in accordance with embodiments of the present disclosure. The example method 400 may be performed to treat or alleviate symptoms of an enlarged prostate gland, which may be caused by a variety of conditions, including but not limited to benign prostatic hyperplasia and/or benign prostatic hypertrophy, along with cancerous conditions that increase the size of the prostate gland, for example via tumor formation. The method may be implemented by one or more of the disclosed devices, systems, and/or components thereof. One or more additional steps may be included, and certain steps may also be omitted or performed in a different sequence than depicted.

In the embodiment shown, the method 400 begins at step 402 by "positioning an elongate portion of a delivery device in a prostatic urethra." The elongate portion may comprise an elongate tubular member defining a lumen through which a disclosed implant, as a complete assembly or as multiple components that are later coupled, is extended together with a disclosed push member. Step 404 may involve "advancing a prostatic implant through the elongate portion of the delivery device, the prostatic implant comprising a distal anchor portion connected to a middle portion." The distal anchor portion of the implant may include a distal piercing portion and a tail portion, the latter of which may include one or more (e.g., two) biased tail members. Step 406 of the method 400 may involve "penetrating a lobe of a prostate gland with a distal piercing portion of the distal anchor portion, the distal piercing portion urged through the lobe by a tubular push member." Embodiments may involve advancing the distal anchor portion, with the middle portion in tow, into and through the prostate tissue via distal advancement of the push member contacting, and thus urging distally, the proximal side of the distal piercing portion. The tail portion may be housed within the lumen of the push member, where the tail members are constrained in a compact delivery configuration. Step 408 may involve "advancing the distal anchor portion through the lobe of the prostate gland until the distal anchor portion is positioned outside a prostatic capsule of the lobe." Step 410 may involve "unsheathing a tail portion of the distal anchor portion and the middle portion by retracting the push member in a proximal direction." The tail portion may be unsheathed just before unsheathing of the middle portion, allowing the tail member(s) to flex outwardly against the outer distal surface of the prostatic capsule. Step 412 may involve "tensioning the middle portion." Step 414 may involve "securing a proximal anchor to the middle portion, the proximal anchor configured to engage with a urethral side of the lobe." The surplus middle portion, extending proximally from the secure proximal anchor, may be cut, and the delivery components removed, leaving the implant at the targeted tissue.

EXAMPLES

The above Detailed Description includes references to the accompanying drawings, which form a part of the Detailed Description. The Detailed Description should be read with reference to the drawings. The drawings show, by way of illustration, specific embodiments in which the present accessory devices and associated methods can be practiced. These embodiments are also referred to herein as "examples."

The Detailed Description is intended to be illustrative and not restrictive. For example, the above-described examples (or one or more features or components thereof) can be used in combination with each other. Other embodiments can be used, such as by one of ordinary skill in the art upon reviewing the above Detailed Description. Also, various features or components have been or can be grouped together to streamline the disclosure. This should not be interpreted as intending that an unclaimed disclosed feature is essential to any claim. Rather, inventive subject matter can lie in less than all features of a particular disclosed embodiment. Thus, the following claim examples are hereby incorporated into the Detailed Description, with each example standing on its own as a separate embodiment:

In Example 1, a system for treating benign prostatic hypertrophy or hyperplasia (and/or an otherwise enlarged prostate gland) includes a delivery device comprising an elongate tubular portion extending from a handle, the elongate tubular portion configured to be advanced through a urethra to a prostatic urethra; a prostatic implant assembly within, and extending from a distal end of, a tubular push member positioned within the elongate tubular portion and configured to urge the prostatic implant distally, the prostatic implant comprising a distal anchor portion that anchors to the prostatic capsule of a lobe of a prostate gland. The system may also include a proximal end portion or urethral endpiece that anchors to a urethral side of the lobe. The distal anchor portion may include a distal piercing portion and a proximal tail portion, the distal piercing portion protruding from a distal end of the tubular push member so as to be adapted to pierce the prostatic lobe during delivery, and the proximal tail portion positioned at least partially within the tubular push member during delivery. The distal piercing portion may be adapted to be advanced through the prostatic capsule of the lobe of the prostate gland so that it can anchor on the outside of the prostatic capsule. The proximal tail portion may be biased so as to extend away from a longitudinal axis of the tubular push member when exiting the tubular push member to anchor the distal anchor portion to the prostatic capsule.

In Example 2, the proximal tail portion may include two tail members each biased so as to extend away from the longitudinal axis of the tubular push member upon exiting the tubular push member.

In Example 3, the proximal tail portion may be biased to assume a curved configuration upon exiting the tubular push member.

In Example 4, the tubular push member may include a blunt distal end that abuts a proximal end of the distal piercing portion during delivery.

In Example 5, a cross-sectional diameter of the tubular push member may be approximately equal to or less than a cross-sectional diameter of the proximal end of the distal piercing portion.

In Example 6, the tubular push member may be configured to be retracted proximally relative to the distal anchor portion.

In Example 7, the distal anchor portion and the proximal end portion may be coupled via a middle portion.

In Example 8, the middle portion comprises a suture.

In Example 9, the distal anchor portion may be configured to be secured tightly against the outside of the prostatic capsule by a tension applied by the middle portion.

In Example 10, the distal piercing portion may include a first material composition, and the proximal tail portion may include a second material composition, different than the first.

In Example 11, the second material composition may include one or more elastic polymers or metals.

In Example 12, before exiting the tubular push member, the proximal tail portion may be approximately parallel to the longitudinal axis of the tubular push member.

In Example 13, the system may lack a hollow delivery needle having a sharp distal tip.

In Example 14, the distal piercing portion may include a body defining a sharp distal tip.

In Example 15, a method for treating benign prostatic hypertrophy or hyperplasia involves positioning an elongate portion of a delivery device in a prostatic urethra; advancing a tubular push member coupled with a prostatic implant through the elongate portion of the delivery device, the prostatic implant comprising a distal anchor portion connected to a middle portion, wherein the distal anchor portion comprises a distal piercing portion and a proximal tail portion, the distal piercing portion protruding from a distal end of the tubular push member and the proximal tail portion positioned at least partially within the tubular push member; penetrating a lobe of a prostate gland with the distal piercing portion of the prostatic implant; inserting the distal anchor portion of the prostatic implant through the lobe of the prostate gland until the distal anchor portion is positioned outside a prostatic capsule of the lobe; unsheathing the prostatic implant by retracting the tubular push member in a proximal direction; tensioning the middle portion; and securing a proximal anchor to the middle portion.

In Example 16, the proximal tail portion may extend away from a longitudinal axis of the tubular push member outside the prostatic capsule upon unsheathing of the distal anchor portion.

In Example 17, the proximal tail portion may include two tail members each biased so as to extend away from a longitudinal axis of the tubular push member.

In Example 18, the proximal tail portion may be biased to assume a curved configuration upon exiting the tubular push member.

In Example 19, a cross-sectional diameter of the tubular push member is approximately equal to or less than a cross-sectional diameter of a proximal end of the distal piercing portion.

In Example 20, the tubular push member abuts a proximal end of the distal piercing portion while inserting the distal anchor portion of the prostatic implant through the lobe.

In Example 21, a prostatic implant configured to compress an enlarged prostate includes a distal anchor portion and a proximal end portion connected by a middle portion. The proximal end portion (or urethral endpiece) may be attached or coupled with the middle portion before or during an implantation process, for example after the distal anchor portion is advanced through the targeted prostatic tissue. The distal anchor portion may include a distal piercing portion and a proximal tail portion. The distal piercing portion may include a sharp distal tip configured to penetrate a lobe of the prostate gland, including the firm prostatic capsule. A tubular push member coupled with the prostatic implant is configured to advance the implant distally, led by the distal piercing portion, until the proximal tail portion is positioned outside the prostatic capsule, at which point the tubular push member is retracted proximally, unsheathing the distal anchor portion of the implant. The proximal tail portion is biased such that, upon exiting the tubular push member, the tail portion extends away from a longitudinal axis of the tubular push member, across the outer surface of the capsule.

Closing Notes

Certain terms are used throughout this patent document to refer to particular features or components. As one skilled in the art appreciates, different people may refer to the same feature or component by different names. This patent document does not intend to distinguish between components or features that differ in name but not in function.

For the following defined terms, certain definitions shall be applied unless a different definition is given elsewhere in this patent document. The terms "a," "an," and "the" are used to include one or more than one, independent of any other instances or usages of "at least one" or "one or more." The term "or" is used to refer to a nonexclusive or, such that "A or B" includes "A but not B," "B but not A," and "A and B." All numeric values are assumed to be modified by the term "about," whether or not explicitly indicated. The term "about" generally refers to a range of numbers that one of skill in the art would consider functionally equivalent to the recited value (e.g., having the same function or result). In many instances, the term "about" can include numbers that are rounded to the nearest significant figure. The recitation of numerical ranges by endpoints includes all numbers and sub-ranges within and bounding that range (e.g., 1 to 4 includes 1, 1.5, 1.75, 2, 2.3, 2.6, 2.9, etc. and 1 to 1.5, 1 to 2, 1 to 3, 2 to 3.5, 2 to 4, 3 to 4, etc.). The terms "patient" and "subject" are intended to include mammals, such as for human or veterinary applications. The terms "distal" and "proximal" are used to refer to a position or direction relative to the treating clinician. "Distal" and "distally" refer to a position that is distant from, or in a direction away from, the treating clinician. "Proximal" and "proximally" refer to a position that is near, or in a direction toward, the treating clinician.

The scope of the invention should be determined with reference to the appended claims, along with the full scope of equivalents to which such claims are entitled. In the appended claims, the terms "including" and "in which" are used as the plain-English equivalents of the respective terms "comprising" and "wherein." Also, in the following claims, the terms "including" and "comprising" are open-ended; that is, a device, kit or method that includes features or components in addition to those listed after such a term in a claim are still deemed to fall within the scope of that claim. Moreover, in the following claims, the terms "first," "second" and "third," etc. are used merely as labels, and are not intended to impose numerical requirements on their objects.

The Abstract is provided to allow the reader to quickly ascertain the nature of the technical disclosure. It is submitted with the understanding that it will not be used to interpret or limit the scope or meaning of the claims.

What is claimed is:

1. A system for treating benign prostatic hypertrophy, comprising:

a delivery device comprising an elongate tubular portion extending from a handle, the elongate tubular portion configured to be advanced through a urethra to a prostatic urethra;

a prostatic implant assembly within, and extending from a distal end of, a tubular push member positioned within the elongate tubular portion and configured to urge the prostatic implant assembly distally, the prostatic implant comprising a distal anchor portion that is configured to anchors to a prostatic capsule of a lobe of a prostate gland, and a proximal end portion that anchors to a urethral side of the lobe, wherein the distal anchor portion comprises a distal piercing portion and a proximal tail portion, the distal piercing portion protruding from the distal end of the tubular push member so as to be adapted to pierce the lobe during delivery, and the proximal tail portion positioned at least partially within the tubular push member during delivery, wherein the distal piercing portion is adapted to be advanced through the prostatic capsule of the lobe of the prostate gland so that the distal piercing portion can anchor on the outside of the prostatic capsule, wherein the proximal tail portion is biased so as to extend away from a longitudinal axis of the tubular push member when exiting the tubular push member to anchor the distal anchor portion to the prostatic capsule, wherein the tubular push member comprises a blunt distal end that abuts a proximal end of the distal piercing portion during delivery, and wherein a cross-sectional diameter of the tubular push member is approximately equal to or less than a cross-sectional diameter of the proximal end of the distal piercing portion.

2. The system of claim 1, wherein the proximal tail portion comprises two tail members each biased so as to extend away from the longitudinal axis of the tubular push member upon exiting the tubular push member.

3. The system of claim 1, wherein the proximal tail portion is biased to assume a curved configuration upon exiting the tubular push member.

4. The system of claim 1, wherein the tubular push member is configured to be retracted proximally relative to the distal anchor portion.

5. The system of claim 1, wherein the distal anchor portion and the proximal end portion are coupled via a middle portion.

6. The system of claim 5, wherein the middle portion comprises a suture.

7. The system of claim 5, wherein the distal anchor portion is configured to be secured tightly against the outside of the prostatic capsule by a tension applied by the middle portion.

8. The system of claim 1, wherein the distal piercing portion comprises a first material composition, and the proximal tail portion comprises a second material composition, different than the first.

9. The system of claim 8, wherein the second material composition comprises one or more elastic polymers or metals.

10. The system of claim 1, wherein before exiting the tubular push member, the proximal tail portion is approximately parallel to the longitudinal axis of the tubular push member.

11. The system of claim 1, wherein the system lacks a hollow delivery needle having a sharp distal tip.

12. The system of claim 1, wherein the distal piercing portion comprises a body defining a sharp distal tip.

13. A method for treating benign prostatic hypertrophy, comprising:

positioning an elongate portion of a delivery device in a prostatic urethra;

advancing a tubular push member coupled with a prostatic implant through the elongate portion of the delivery device, the prostatic implant comprising a distal anchor portion connected to a middle portion, wherein the distal anchor portion comprises a distal piercing portion and a proximal tail portion, the distal piercing portion protruding from a distal end of the tubular push member and the proximal tail portion positioned at least partially within the tubular push member;

penetrating a lobe of a prostate gland with the distal piercing portion of the prostatic implant;

inserting the distal anchor portion of the prostatic implant through the lobe of the prostate gland until the distal anchor portion is positioned outside a prostatic capsule of the lobe;

unsheathing the prostatic implant by retracting the tubular push member in a proximal direction;

tensioning the middle portion; and securing a proximal anchor to the middle portion, wherein the tubular push member comprises a blunt distal end that abuts a proximal end of the distal piercing portion during delivery, and wherein a cross-sectional diameter of the tubular push member is approximately equal to or less than a cross-sectional diameter of the proximal end of the distal piercing portion.

14. The method of claim 13, wherein the proximal tail portion extends away from a longitudinal axis of the tubular push member outside the prostatic capsule upon unsheathing of the distal anchor portion.

15. The method of claim 13, wherein the proximal tail portion comprises two tail members each biased so as to extend away from a longitudinal axis of the tubular push member.

16. The method of claim 13, wherein the proximal tail portion is biased to assume a curved configuration upon exiting the tubular push member.

17. The method of claim 13, wherein the tubular push member abuts the proximal end of the distal piercing portion while inserting the distal anchor portion of the prostatic implant through the lobe.

* * * * *